(12) United States Patent
Madigan et al.

(10) Patent No.: US 7,205,535 B2
(45) Date of Patent: Apr. 17, 2007

(54) ELEMENTAL GAMMA RAY SIGNATURE INSTRUMENT

(75) Inventors: William Madigan, Houston, TX (US); Richard Pemper, Sugar Land, TX (US); Pingjun Guo, Pearland, TX (US)

(73) Assignee: Baker Hughes Incorporated, Houston, TX (US)

( * ) Notice: Subject to any disclaimer, the term of this patent is extended or adjusted under 35 U.S.C. 154(b) by 158 days.

(21) Appl. No.: 10/916,921

(22) Filed: Aug. 12, 2004

(65) Prior Publication Data

US 2006/0033022 A1   Feb. 16, 2006

(51) Int. Cl.
G01V 5/10 (2006.01)

(52) U.S. Cl. .................................. 250/269.6
(58) Field of Classification Search .............. 250/269.6
See application file for complete search history.

(56) References Cited

U.S. PATENT DOCUMENTS

| | | | | |
|---|---|---|---|---|
| 4,390,783 A | | 6/1983 | Grau | 250/270 |
| 4,394,574 A | | 7/1983 | Grau et al. | 250/262 |
| 4,712,424 A | | 12/1987 | Herron | 73/152 |
| 4,773,264 A | * | 9/1988 | Herron | 73/152.05 |
| 4,916,616 A | * | 4/1990 | Freedman et al. | 702/13 |
| 5,440,118 A | * | 8/1995 | Roscoe | 250/269.6 |
| 5,471,057 A | | 11/1995 | Herron | 250/269.6 |
| 5,675,147 A | * | 10/1997 | Ekstrom et al. | 250/256 |

OTHER PUBLICATIONS

Peter Westaway et al.; *Neutron-Induced Gamma Ray Spectroscopy for Reservoir Analysis*, SPE-9461, Jun. 1983, pp. 553-564, 12 Figs., 3 Tables.
R.C.Hertzog;*Laboratory and Field Evaluation of an Inelastic-Neutron-Scattering and Capture Gamma Ray Spectroscopy Tool*,SPE 7430, 53rd Annual Fall Technical Conference and Exhibition of the Society of Petroleum Engineers of AIME, Oct. 1-3, 1978; pp. 1-14, 18 Figs.
J. A. Grau et al.; *Prompt γ-Ray Spectral Analysis of Well Data Obtained with NaI(Tl) and 14 MeV Neutrons*, Nucl. Geophys. vol. 1, No. 2, pp. 157-165, 19879 Figs., 3 Tables.
B. A. Roscoe et al.; *Statistical Precision of Neutron-Induced Gamma Ray Spectroscopy Measurements*, The Log Analyst, Nov.-Dec., 1987, pp. 538-545, 10 Figs.

* cited by examiner

*Primary Examiner*—Constantine Hannaher
(74) *Attorney, Agent, or Firm*—Madan, Mossman & Sriram, P.C.

(57) ABSTRACT

Elemental analysis of an earth formation is obtained using measurements from a gamma ray logging tool. From the elemental analysis, an estimate of the mineralogy of the formation is made treating the problem as one of Linear Programming (maximizing an objective function subject to equality and/or inequality constraints).

32 Claims, 3 Drawing Sheets

ELEMENTAL GAMMA RAY SIGNATURE INSTRUMENT

BACKGROUND OF THE INVENTION

1. Field of the Invention

The present invention is in the field of gamma ray testing of geological formations. In particular, the invention determines the mineralogy of a formation from recorded spectra.

2. Description of the Related Art

Well logging systems have been utilized in hydrocarbon exploration for many years. Such systems provide data for use by geologists and petroleum engineers in making many determinations pertinent to hydrocarbon exploration. In particular, these systems provide data for subsurface structural mapping, defining the lithology of subsurface formations, identifying hydrocarbon-productive zones, and interpreting reservoir characteristics and contents. Many types of well logging systems exist which measure different formation parameters such as conductivity, travel time of acoustic waves within the formation and the like.

One class of systems seeks to measure incidence of nuclear particles on the well logging tool from the formation for purposes well known in the art. These systems take various forms, including those measuring natural gamma rays from the formation. Still other systems measure gamma rays in the formation caused by bursts of neutrons into the formation by a neutron source carried by the tool and pulsed at a preselected interval.

In these nuclear well logging systems, reliance is made upon the physical phenomenon that the energies of gamma rays given off by nuclei resulting from natural radioactive decay or induced nuclear radiation are indicative of the presence of certain elements within the formation. In other words, formation elements will react in predictable ways, for example, when high-energy neutrons on the order of 14.2 MeV collide with the nuclei of the formation elements. Different elements in the formation may thus be identified from characteristic gamma ray energy levels released as a result of this neutron bombardment. Thus, the number of gamma rays at each energy level will be functionally related to the quantity of each element present in the formation, such as the element carbon, which is present in hydrocarbons. The presence of gamma rays at a 2.2 MeV energy level may for example, indicate the presence of hydrogen, whereas predominance of gamma rays having energy levels of 4.43 and 6.13 MeV, for example, may indicate the presence of carbon and oxygen respectively.

In these nuclear well logging systems, it is frequently useful to obtain data regarding the time spectral distributions of the occurrence of the gamma rays. Such data can yield extremely valuable information about the formation, such as identification of lithologies that are potentially-hydrocarbon producing. Moreover, these desired spectral data may not only be limited to that of natural gamma rays, for example, but also may be desired for the gamma ray spectra caused by bombardment of the formation with the aforementioned pulsed neutron sources.

Well logging systems for measuring neutron absorption in a formation use a pulsed neutron source providing bursts of very fast, high-energy neutrons. Pulsing the neutron source permits the measurement of the macroscopic thermal neutron absorption capture cross-section $\Sigma$ of a formation. The capture cross-section of a reservoir rock is indicative of the porosity, formation water salinity, and the quantity and type of hydrocarbons contained in the pore spaces.

The measurement of neutron population decay rate is made cyclically. The neutron source is pulsed for 20–40 microseconds to create a neutron population. Neutrons leaving the pulsed source interact with the surrounding environment and are slowed down. In a well logging environment, collisions between the neutrons and the surrounding fluid and formation atoms act to slow these neutrons. Such collisions may impart sufficient energy to these atoms to leave them in an excited state, from which after a short time gamma rays are emitted as the atom returns to a stable state. Such emitted gamma rays are labeled inelastic gamma rays. As the neutrons are slowed to the thermal state, they may be captured by atoms in the surrounding matter. Atoms capturing such neutrons are also caused to be in an excited state, and after a short time gamma rays are emitted as the atom returns to a stable state. Gamma rays emitted due to this neutron capture reaction are labeled capture gamma rays. In wireline well logging operations, as the neutron source is pulsed and the measurements made, the subsurface well logging instrument is continuously pulled up through the borehole. This makes it possible to evaluate formation characteristics over a range of depths.

Depending on the material composition of the earth formations proximal to the instrument, the thermal neutrons can be absorbed, or "captured", at various rates by certain types of atomic nuclei in the earth formations. When one of these atomic nuclei captures a thermal neutron, it emits a gamma ray, which is referred to as a "capture gamma ray".

Prior art methods exist for determining attributes of a formation from logging results. For example, U.S. Pat. No. 4,712,424, to Herron, performs an elemental analysis of core data as well as a mineralogical analysis. Based on a regression analysis of the core data, an element-mineral transformation matrix is determined. This predetermined transformation matrix is then applied to elemental analysis made from nuclear logs in an earth formation.

There are several problems with the Herron method. First is the problem of sampling: there is no such thing as a universal transformation matrix that will convert any elemental analysis, regardless of geologic setting, into a mineralogical analysis. The transformation matrix therefore has to be derived on a sample that is truly representative of the earth formation to which the matrix is being applied. This is not an easy task, and there still remains the problem of knowing when a particular transformation matrix is being applied to data for which it is not suitable. Detailed mineralogical and elemental analysis of a wide variety of core samples is not an easy task. A second issue has to do with the actual inversion, and the fact that physically unrealistic mineralogical analyses may result, specifically in the form of negative values of a mineral. Such negative values are indications that either the matrix is being applied beyond its range of applicability or the elemental analysis may be incorrect, or both may be occurring.

U.S. Pat. No. 4,394,574, to Grau et al., discusses investigating the composition of a geological formation traversed by a borehole by measuring an energy spectrum of the radiation within the borehole. The measured spectrum is thereafter analyzed by comparing it with a composite spectrum, made up of standard spectra of constituents postulated to comprise the formation-borehole system. As a result of such analysis, the proportions of the postulated constituents in the formation are determined.

U.S. Pat. No. 4,390,783, to Grau, discusses an iterative technique in which the offset of the background spectrum is varied until a goodness of fit parameter is optimized. The magnitude of the background spectrum is normalized by the ratio of the number of background counts in the gross energy spectrum to the number of counts in the background spectrum. Subsequently, the background spectrum is normalized by the ratio and then subtracted from the gross inelastic spectrum in order to determine a net inelastic spectrum.

Methods of decomposing obtained spectra into constituent spectra have been discussed, for instance, in SPE 7430 "Laboratory and Field Evaluation of an Inelastic-Neutron-Scattering and Capture Gamma Ray Spectroscopy Tool", 1978., by Hertzog, SPE9461, 1980; SPE "Prompt Gamma-Ray Spectral Analysis of Well Data Obtained with NaI(T1) and 14 MeV Neutrons," 1986, by Grau and Schweitzer; and Neutron-Induced Gamma Ray Spectroscopy for Reservoir Analysis, June 1983, by Westaway et al. The methods discussed in these papers correct an obtained inelastic spectrum by subtracting a background spectrum. Statistical analysis of obtained spectra is discussed in "Statistical Precision of Neutron-Induced Gamma Ray Spectroscopy Measurements" by Roscoe et al., November-December, 1987, The Log Analyst.

U.S. Pat. No. 5,471,057, to Herron, discusses a method for determining the elemental concentrations in an underground formation by irradiating the formation with neutrons, detecting the γ ray spectrum arising from neutron capture by the formation and analyzing the spectrum to determine relative elemental yields which are converted to elemental concentrations. This method avoids the need for activation measurements or natural radiation measurements and is made possible by applying a factor to modify the determined yield of iron (Fe) from the spectrum to compensate for the absence of measurement of aluminum (Al) and for the absence of potassium (K) when not measured directly. The apparatus of Herron '057 can comprise a neutron source, such as a broad energy chemical source, e.g. AmBe, or a pulsed accelerator source, a γ ray detector for detecting capture γ rays and means for analyzing the spectra detected by the determining the elemental concentrations in the formation.

There is a need for a more complete analysis of the obtained gamma ray spectra. A separation of inelastic and capture gamma ray spectra yields a more complete understanding of the elemental composition of a geological structure. Consequently, an advantage can be obtained through a combined analysis of both inelastic and capture spectra in terms of their formation constituents. Such a method should not give physically unrealistic analyses. The present invention fulfills this need.

SUMMARY OF THE INVENTION

One embodiment of the present invention is a method of determining a mineralogical composition of an earth formation. An elemental analysis of the earth formation is obtained using measurements made by logging tool conveyed in a borehole in an earth formation. A set of possible mineral constituents for the earth formation is defined. The mineralogical composition is determined by solving a constrained optimization problem to determine a relative fraction of each of the possible mineral constituents that would give the obtained elemental composition. The logging tool may be a gamma ray logging tool in which a neutron source, such as a pulsed neutron source, is used to irradiate the earth formation, and gamma rays resulting from interaction of the neutrons with nuclei in the formation are detected using one or more detectors spaced apart from the neutron source.

Capture and inelastic gamma ray spectra are determined from the detected radiation. Elemental composition may be obtained using a decomposition of the capture and inelastic gamma ray spectra using known basis functions for a specified list of elements. The determined elemental composition may be based on one or both of the sets of spectra. The possible mineral constituents of the rock may be prepared on the basis of one or more sources of geologic information (e.g., basin wide, prospect wide, or from sequence stratigraphy) and petrophysical information. The basic concept of sequence stratigraphy is that the sequence of an earth formation at any location follows certain well established rules, so that prediction of properties of the rock can be made based on knowledge of formations above and below, knowledge of the position of the formation in a sedimentary basin and by analysis of seismic data. The literature on the subject is too diverse to discuss in further detail. The 2003-2004 AAPG Distinguished Lecture of J. F. Sarg discusses carbonate sequence stratigraphy in broad terms.

The determination of mineralogical composition from the elemental composition is treated as a constrained optimization problem. For example, Linear Programming (LP) may be used in which the total mineral composition using the list of minerals is maximized. Equality and/or inequality constraints are included to make the solution physically realistic, e.g., by requiring that the fraction of each mineral be non-negative. Slack variables may be included in the LP formulation. The mineralogical composition of a carbonate formation could be indicative of the amount of dolomitization that may have occurred.

The logging tool may be conveyed in the borehole on a wireline, slickline, or may be part of a logging-while-drilling (LWD) assembly conveyed on a drilling tubular. The processing may be done by downhole or surface processors or a combination thereof.

BRIEF DESCRIPTION OF THE DRAWINGS

The present invention is best understood with reference to the accompanying figures in which like numerals refer to like elements and in which.

DETAILED DESCRIPTION OF THE INVENTION

Figure 1:
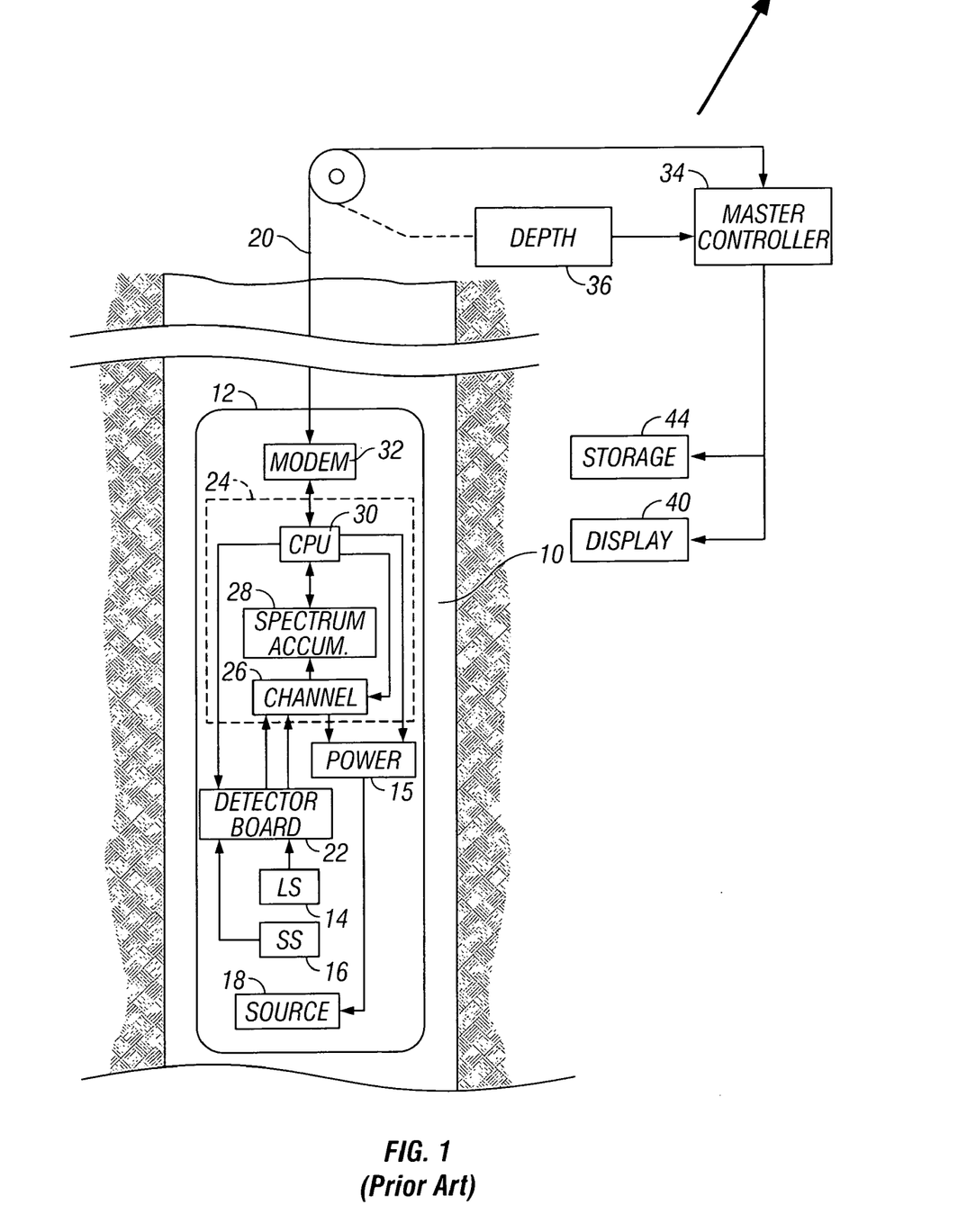
FIG. 1 (Prior Art) illustrates a nuclear well logging configuration in accordance with the present invention.

Referring now to the drawings in more detail, and particularly to FIG. 1, there is illustrated a nuclear well logging configuration in accordance with the present invention. Well 10 penetrates the earth's surface and may or may not be cased depending upon the particular well being investigated. Disposed within well 10 is subsurface well logging instrument 12. The system diagramed in FIG. 1 is a microprocessor-based nuclear well logging system using multi-channel scale analysis for determining the timing distributions of the detected gamma rays. Well logging instrument 12 includes long-spaced (LS) detector 14, short-spaced (SS) detector 16 and pulsed neutron source 18. In an exemplary embodiment, LS and SS detectors 14 and 16 are comprised of bismuth-germanate (BGO) crystals coupled to photomultiplier tubes. To protect the detector systems from the high temperatures encountered in boreholes, the detector system may be mounted in a Dewar-type flask. Also, in an exemplary embodiment, source 18 comprises a pulsed neutron source using a D-T reaction wherein deuterium ions are accelerated into a tritium target, thereby generating neutrons having an energy of approximately 14 MeV. The filament current and accelerator voltage are supplied to source 18 through power supply 15. Cable 20 suspends instrument 12 in well 10 and contains the required conductors for electrically connecting instrument 12 with the surface apparatus.

The outputs from LS and SS detectors 14 and 16 are coupled to detector board 22, which amplifies these outputs and compares them to an adjustable discriminator level for passage to channel generator 26. Channel generator 26 converts the output pulse heights to digital values, which are accumulated into pulse height spectra, in which the pulses are sorted according to their amplitudes into a discrete array of bins. The bins uniformly divide the entire amplitude range. These pulse height spectra are accumulated in registers in the spectrum accumulator 28, the spectra being sorted according to their type: inelastic, capture, or background. After a pulse height spectrum has been accumulated, CPU 30 controls the transfer of the accumulated data to the modem 32, which is coupled to cable 20 for transmission of the data over a communication link to the surface apparatus. To be explained later are further functions of CPU 30 in communicating control commands which define certain operational parameters of instrument 12 including the discriminator levels of detector board 22, and the filament current and accelerator voltage supplied to source 18 by power supply 15.

The surface apparatus includes master controller 34 coupled to cable 20 for recovery of data from instrument 12 and for transmitting command signals to instrument 12. There is also associated with the surface apparatus depth controller 36 which provides signals to master controller 34 indicating the movement of instrument 12 within well 10. An input terminal may be coupled to master controller or processor 34 to allow the system operator to provide selected input into master controller 34 for the logging operation to be performed by the system. Display unit 40, and storage unit 44 coupled to the master controller 34 may be provided. The data may also be sent by a link to a remote location. Processing may be done either by the surface processor, at the remote site, or by a downhole processor.

In a well logging operation such as is illustrated by FIG. 1, master controller 34 initially transmits system operation programs and command signals to be implemented by CPU 30, such programs and signals being related to the particular well logging operation. Instrument 12 is then caused to traverse well 10 in a conventional manner, with source 18 being pulsed in response to synchronization signals from channel generator 26. Typically, source 18 is pulsed at a rate of 10,000 bursts/second (10 kHz). This, in turn, causes a burst of high-energy neutrons on the order of 14 MeV to be introduced into the surrounding formation to be investigated. In a manner previously described, this population of high energy neutrons introduced into the formation will cause the generation of gamma rays within the formation which at various times will impinge on LS and SS detectors 14 and 16. As each gamma ray thus impinges upon the crystal-photomultiplier tube arrangement of the detectors, a voltage pulse having an amplitude functionally related to the energy of the particular gamma ray is delivered to detector board 22. It will be recalled that detector board 22 amplifies each pulse and compares it to an adjustable discriminator level, typically set at a value corresponding to approximately 100 keV. If such pulse has an amplitude corresponding to an energy of at least approximately 100 keV, the voltage pulse is transformed into a digital signal and passed to channel generator 26 of MCS section 24.

Figure 2:
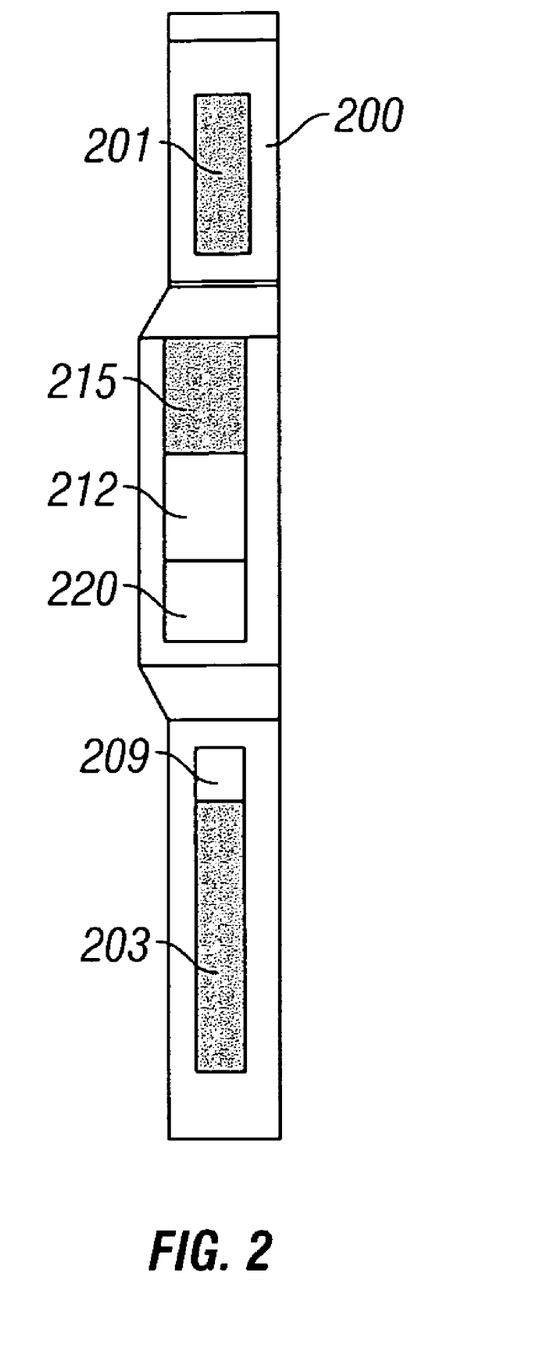
FIG. 2 shows an instrument suitable for use with the present invention.

FIG. 2 illustrates a schematic diagram of an instrument suitable for use with the present invention. The Elemental Neutron Spectrometer (ENS™) is a wireline instrument designed to provide formation mineralogical information, shale identification, and clay typing. The enhanced mineralogical data obtained from the ENS also enables enhanced porosity measurements. The present invention is usable in open hole wireline logging. In a typical embodiment, the present invention uses the ECLIPS™ acquisition system of Baker Hughes Incorporated. Alternatively, the present invention can be used, for example, with the FOCUS system of Baker Hughes, Incorporated. Also, under most conditions, the ENS can be run in combination with Gamma Ray/Spectralog, Neutron, and Density nuclear tools. The ENS utilizes an axial pulsed neutron generator of the same type as that used in the reservoir performance monitor instruments. Thus, there are no special storage or transportation requirements except those of a regulatory nature associated with pulsed neutron generators. The logging speed is dependent upon the environment. A typical logging speed is in the range of 15–30 ft/min.

The ENS measurement device of FIG. 2 employs the principle of neutron-induced gamma ray spectroscopy. ENS component parts are encapsulated within wireline device casing 200. The neutron source of the present invention is typically a pulsed neutron source. The use of a pulsed neutron source is advantageous over the use of a chemical neutron source due to its ability to operate over a broader range of frequencies. Neutron source 209 discharges high-energy bursts of neutrons into the surrounding formation. The electronic pulsed neutron generator is typically operated at a rate of approximately 10,000 Hz, so that each burst takes place within a 100 microsecond window. Gamma rays produced via interaction of the discharged neutrons and the formation are detected at the scintillation detector 212 attached to acquisition and telemetry electronics 215. Power supply 201 enables the ENS device. Electronics 203 enables the neutron source. A neutron shield 220 attenuates the neutron flux propagating directly from the source to the detector.

Figure 3:
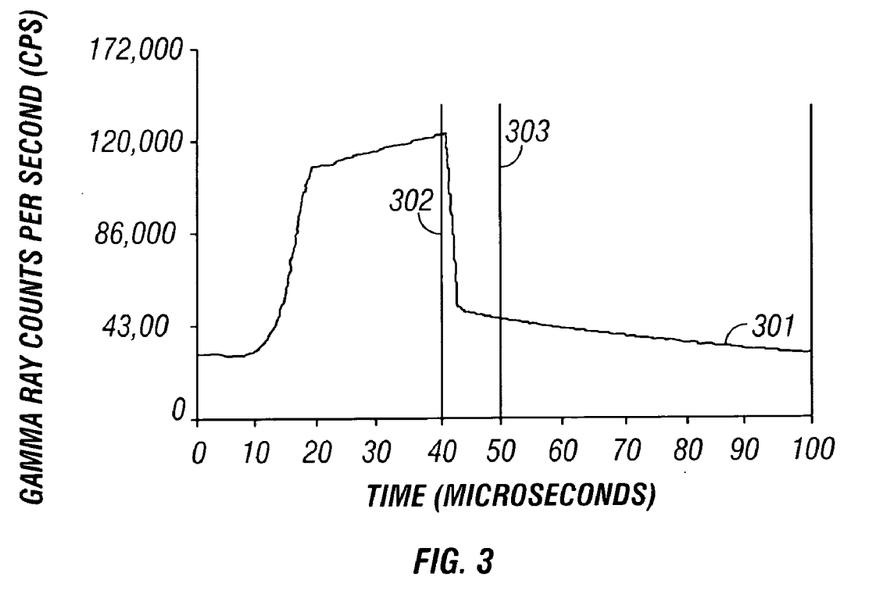
FIG. 3 shows the basic timing of the pulsed neutron source and the produced gamma rays.

FIG. 3 illustrates the basic timing of the pulsed neutron source and the produced gamma rays. Time is displayed along the x-axis in microseconds. The gamma ray counts per second (cps) is displayed along the y-axis. The neutron burst defines a first-detector-gate interval, referred to as the "burst gate" or inelastic gate. Typically a total spectrum of gamma rays resulting from both inelastic neutron scattering and capture gamma ray scattering are produced during the active duration of the neutron source, and the timing of the inelastic gate enables obtaining the total spectrum. In the example of FIG. 3, the number of counts rises significantly (typically to 120 kcps) during the inelastic gate, which extends approximately from 10 μsec to 40 μsec. The deactivation of the neutron source causes the inelastic gamma rays to disappear from the count almost immediately. A "background gate" 302–303 is shown at a point substantially coincident with deactivation of the neutron source. The background gate of FIG. 3 extends approximately from 40 μsec to 50 μsec. The counts obtained during the background gate are attributable to background gamma rays, but also to capture gamma rays, which make up a significant portion of the spectrum during the background gate. The background gate is followed by a "capture gate" 301. The capture gate contains gamma rays substantially due to captured neutrons of the surrounding formation.

In an exemplary embodiment of the present invention, energized neutrons are injected from a pulsed neutron source 209 into a surrounding formation. The scintillation detector records the spectrum over a predetermined time interval. During the inelastic gate, a total spectrum of gamma rays is obtained from the formation layer. During a capture gate, a capture spectrum of gamma rays is obtained from the formation layer. A determinable factor of the capture spectrum can be subtracted from the obtained total spectrum to derive a spectrum substantially representative of an inelastic spectrum only. The elemental contribution to the inelastic spectrum and the capture spectrum can then be determined by determining a first constituent spectrum from the inelastic spectrum and a second constituent spectrum from the capture spectrum. An operator versed in the arts can then use the determined elemental contributions to determine a parameter of the surrounding formation.

Figure 4:
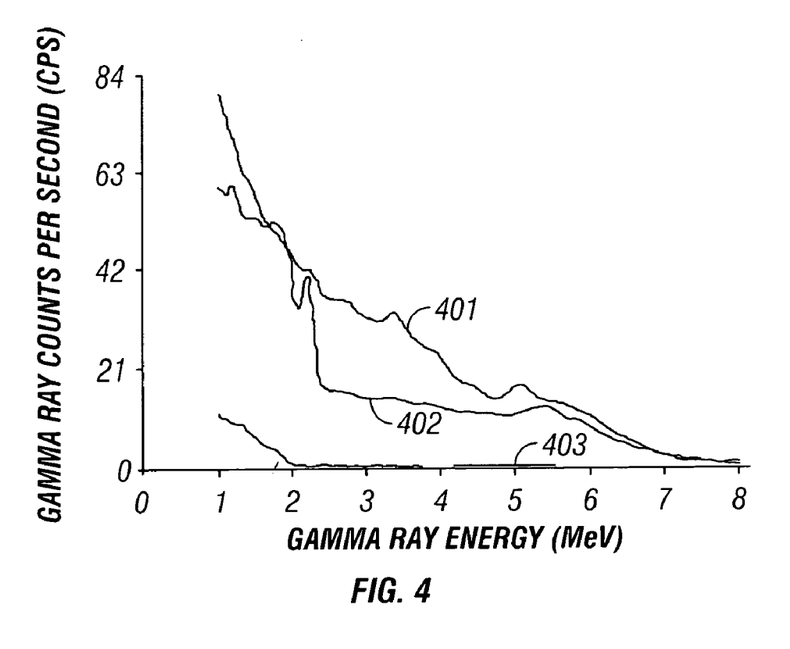
FIG. 4 shows capture and inelastic spectra from limestone formation with oil-filled borehole.

The derived gamma ray energy spectra for data analysis comprise both the capture spectrum and the inelastic spectrum. An inelastic gamma ray is generated from the nucleus of the atom from which there is a scattering of initial highly energetic neutrons. A capture gamma ray is emitted by the nucleus of an atom through absorption of a neutron after its energy has diminished. FIG. 4 shows capture and inelastic spectra from limestone formation with oil-filled borehole. The three spectra are the inelastic spectrum 401, the capture spectra 402, and the background spectrum 403.

A novel feature of the present invention is the analysis of separate inelastic and capture spectra in terms of their constituent spectra. Prior art discusses methods for removing the effects of a capture spectrum from a total spectrum obtained during a burst gate, consequently obtaining an improved inelastic spectrum. A corrected fraction of the capture spectrum is subtracted from the total spectrum in order to generate a representative inelastic spectrum. The corrected fraction is referred to as the capture subtraction factor. The method for calculating this value comprises using a capture gamma ray response function to estimate the capture and inelastic components within a recorded time spectrum. Analysis of the spectra can be performed uphole or downhole using a processor or expert system.

A library of elemental basis functions can be used to enable a decomposition of at least one of capture and inelastic spectra into their respective constituent spectra. A partial list of elements includes Ca, Cl, Fe, Mg, Si. Currently, constituent spectra representing 20 elements are usable in the present invention. When the fraction of a particular element obtained from both the capture and inelastic spectrum are reasonably close, then their average value may be used for the elemental analysis. Large differences between estimates for a particular element obtained by capture and inelastic spectral decomposition should serve as a cautionary flag. As part of the spectral decomposition using basis functions, it is standard practice to also estimate uncertainties along with the regression coefficients. These uncertainties can be used to provide an estimate of the amount of an element from the individual estimates obtained from inelastic and capture spectra. The number of elements can be increased and is not meant as a limitation of the present invention. Elemental basis functions could further be produced using various methods. For example, use of a computer can enable generation of an elemental basis function of a previously unlisted element.

The elements that can be readily measured from the capture gamma ray energy spectrum comprise Ca, Cl, H, Fe, Mg, Si, and S. The elements that can be readily measured from the inelastic gamma ray energy spectrum comprise C, Ca, Fe, Mg, O, Si, and S. The list is not intended to be complete and other elements could also be identified. Table 1 summarizes the appearance of several elements readily identifiable in both capture and inelastic spectra. In some cases, the same element can be found in both the capture and inelastic spectra. Those elements found in both the capture and inelastic spectra further aid a log analyst in the final scientific interpretation of the data.

TABLE 1

| Element | Capture Spectrum | Inelastic Spectrum |
| --- | --- | --- |
| Carbon | | C |
| Calcium | Ca | Ca |
| Chlorine | Cl | |
| Hydrogen | H | |
| Iron | Fe | Fe |
| Magnesium | Mg | Mg |
| Oxygen | | O |
| Silicon | Si | Si |
| Sulfur | S | S |

Once a gamma ray spectrum is extracted for an individual element, it can be used as an elemental standard. These standards are determinable, for example, using a combination of empirical data from known formations in the Nuclear Instrument Characterization Center, and using computer simulations employing detailed physical modeling techniques. The combination of these standards that results in the best fit to the measured spectra determines the elemental yields.

Mineral identification can be derived from elemental yields. Some typical mineral compositions are listed in Table 2.

TABLE 2

| Category | Formation Type | Mineral Composition |
| --- | --- | --- |
| General | Sandstone | $SiO_2$ |
| | Shale | — |
| Clay | Kaolinite | $Al_2O_3$—$2SiO_2$—$2H_2O$ |
| | Smectite | $Si_4O_{10}(OH)_2$—$nH_2O$ |
| Carbonate | Limestone | $CaCO_3$ |
| | Dolomite | $CaMg(CO_3)_2$ |
| | Siderite | $FeCO_3$ |
| Sulfate | Anhydrite | $CaSO_4$ |
| Oxide | Magnetite | $Fe_3O_4$ |
| | Quartz | $SiO_2$ |
| Mica | Biotite | $K(Mg,Fe)_3(Al,Fe)Si_3O_{10}(OH,F)_2$ |

Various pattern recognition algorithms can be used to decipher the elemental concentrations measured during a logging run. Alternatively, signature recognition methods can be used to decipher elemental concentrations. An example of such patterns can be observed in Table 3, in which similar measurements were made during a feasibility study. The formations measured for the example of Table 3 possess zero porosity and a 7⅞-inch borehole. An operator versed in the arts can use information from Table 3 for determination of mineral type. As an example, sandstone can be distinguished from limestone. Note, for example, that the 0 pu sandstone formation shows large fractions of silicon whereas the corresponding limestone and dolomite formations do not. As a further example, the magnesium signature in the dolomite formation enables an operator to distinguish dolomite from limestone.

TABLE 3

| Spectrum | Formation | C | Ca | Fe | H | Mg | O | Si |
|---|---|---|---|---|---|---|---|---|
| Capture | Dolomite | | 0.62 | 0.02 | 0.24 | 0.10 | | 0.03 |
| Capture | Limestone | | 0.75 | 0.00 | 0.23 | 0.00 | | 0.00 |
| Capture | Sandstone | | 0.01 | 0.01 | 0.35 | 0.02 | | 0.63 |
| Inelastic | Dolomite | 0.07 | 0.18 | | | 0.06 | 0.43 | 0.04 |
| Inelastic | Limestone | 0.08 | 0.40 | | | 0.00 | 0.37 | 0.00 |
| Inelastic | Sandstone | 0.00 | 0.01 | | | 0.01 | 0.34 | 0.51 |

One embodiment of the invention is based on recognition that going from Table 1 (the elemental analysis) to Table 2 (the mineralogical makeup of the rock) can be analyzed as a problem in Linear Programming (LP). The LP problem can be formulated as follows:

Maximize an objective function z:

$$z = \sum_{j=1}^{m} X_j \quad (1)$$

subject to a set of n constraints (linear inequalities) of the general form:

$$b_i \geq \sum_{j=1}^{m} a_{ij} X_j, \quad (i = 1, n) \quad (2)$$

and to a set of m basic constraints (linear inequalities) of the form:

$$X_j \geq 0 (j=1,m) \quad (3).$$

In the context of the present invention, $X_j$ is the abundance of mineral j in the rock, $b_i$ is the amount element i in the rock, and $a_{ij}$ is the weight ratio of element i in mineral j. The use of the basic (non-negativity) constraints given by eqn. (3) clearly distinguishes this method from the regression analysis used by Herron in which physically unrealistic results are possible in the absence of such constraints.

Eqn. (1) dictates that the total mineral abundance be maximized. It is to be noted that LP can also be used to minimize an objective function. Ideally, if all the elements have been analyzed with absolute accuracy, and if the presence and exact composition of all the minerals in the rock were known, the z should be equal to 100% by weight. In practice, z may be less than 100%. Eqn. (2) is made up of greater-than-or-equal-to ($\geq$) relationships. This accounts for the possibility that a fraction of the elements may be tied up either in minerals not considered, or in amorphous or organic phases.

In the real world, the constraints can be a mixture of inequality constraints ($\geq$, $\leq$) as well as equality constraints. Eqn. (3) simply requires that the amount of a mineral cannot be negative. Solution of eqns. (1)–(3) is a standard problem in Linear Programming and can be found in any textbook on the subject. The most commonly used method for solving LP problems is the Simplex method.

A related problem using a related method is solved in Caritat et al. "LPNORM: A Linear Programming Normative Analysis Code". The problem solved in Caritat is to determine the mineralogy of a rock, but instead of starting with an elemental analysis, the starting point includes measurements of relative abundance of oxides. In the example shown in Caritat, the basic measurements are of the relative oxide abundance, specifically abundance of $SiO_2$, $Al_2O_3$, $Fe_2O_3$, MgO and $K_2O_3$. Given this oxide constituent analysis, the relative fractions of quartz, kaolinite, chlorite and illite were determined. The composition of quartz and kaolinite is fixed (quartz being $SiO_2$ while kaolinite is $Al2Si_2O_5(OH)_4$. Chlorite and illite can have variable elemental composition, but Caritat assumes illite and chlorite to be $K_{0.96}Fe_{0.31}Mg_{0.28}Al_{1.97}Si_{3.46}O_{10}(OH)_2$ and $Fe_3Mg_2Al_2Si_3O_{10}(OH)_8$ respectively. For this particular example, Caritat shows that a modified LP problem referred to as LPNORM solution works satisfactorily.

The modification made to the standard LP problem in the implementation of LPNROM is the replacement of inequality constraints given by eqns. (2) and (3) by equalities by using auxiliary variables. Specifically, in LPNORM, the objective function is of the form:

$$z = \sum_{j=1}^{m} X_j - \sum_{i=1}^{n} \lambda_i \quad (5)$$

subject to a set of n constraints of the form $$b_i \geq \sum_{j=1}^{m} a_{ij} X_j, +\lambda_i \quad (i = 1, n) \quad (6)$$

and to a set of m+n basic constraints $$X_j \geq 0 (j=1,m); \lambda_i \geq 0, (i=1,n). \quad (7)$$

where the $\lambda_i$ are slack variables. The slack variable represents the amount of any element that cannot be accounted for. The sum of the slack variables is an indication of how well the mineral composition of the rock fits the elemental composition.

It should be emphasized that conceptually, for the purposes of the LP method, there is no difference going from an oxide analysis to a mineralogy, as was done by Caritat, or in going from an elemental analysis to a mineralogy as is done in the present invention. In the context of formation evaluation, most of the earth formations encountered in the earth fall into one of three categories: sandstones, carbonates, and clay (or shale minerals). Reservoir rocks are typically either sandstones or carbonates, the latter being further subdivided into limestone and dolomite. In the process of dolomitization, magnesium ions replace calcium ions in calcite, forming the mineral dolomite. The size of the magnesium atom is less than that of the calcium atom, so the replacement of calcite by dolomite in a rock increases the pore space in the rock by 13%. Consequently, dolomites are an important reservoir rock. The dolomitization can be partial or complete, so that knowledge of the relative fractions of dolomite and calcite in a particular rock is useful in evaluating its reservoir potential. This is done in the method of the present invention.

In sandstone reservoirs, it is common to find clay minerals that can greatly reduce the permeability of the rock with little effect on porosity. The amount of clay minerals can be determined from a natural gamma ray log (that measures the radioactivity of potassium in the clay minerals). The method of the present invention provides additional information about the presence of clay minerals in sand formations without having to run permeability tests that are time consuming.

In applying the method of the present invention, use is made of as much a priori information as possible in defining the possible list of minerals that are to be identified. This information can come from geologic and petrophysical information. The geologic information can come from either on a basin wide scale, or on a prospect scale (from other wells). Information can also come from the same well using sequence stratigraphy principles. This can help exclude certain minerals. For example, in carbonate rocks, due to the geologic setting in which they are formed, in most instances $SiO_2$ can be ruled out as a possible mineral and the most likely minerals are limestone, dolomite and, to a lesser extent, halite, anhydrite and gypsum. Possible presence of clay minerals can be obtained from petrophysical information such as background gamma ray logs. In sedimentary formations, on the other hand, $SiO_2$ and clay minerals are likely to be present, and minerals like limestone, dolomite, halite, anhydrite and gypsum are unlikely to be present. Deletion of extraneous minerals from the candidate minerals greatly speeds up the computation.

The invention has been described in terms of measurements made using logging tools conveyed on a wireline device in a borehole. The method can also be used using data obtained by sensors conveyed on a slickline. The method can also be used on data obtained using measurement-while-drilling sensors conveyed on a drilling tubular.

While the foregoing disclosure is directed to the specific embodiments of the invention, various modifications will be apparent to those skilled in the art. It is intended that all such variations within the scope and spirit of the appended claims be embraced by the foregoing disclosure.

What is claimed is:

1. A method of determining a composition of an earth formation, the method comprising:
   (a) estimating an elemental composition of said earth formation using a logging tool conveyed in a borehole in said earth formation;
   (b) defining a set of possible constituents in said earth formation; and
   (c) solving a constrained optimization problem to determine a fraction of each of said possible constituents that would give said estimated elemental composition, the solution not using an estimate of a shale volume.

2. The method of claim 1 wherein said logging tool further comprises:
   (i) a source of neutrons that propagates neutrons into said earth formation, and
   (ii) at least one detector spaced apart from said source of neutrons that measures gamma rays resulting from interaction of said propagated neutrons with nuclei in said earth formation.

3. The method of claim 2 wherein said at least one detector comprises at least two spaced-apart detectors.

4. The method of claim 2, wherein said neutron source further comprises a pulsed neutron source.

5. The method of claim 1 wherein estimating said elemental composition further comprises determining (i) a capture spectrum of gamma rays, and, (ii) an inelastic spectrum of gamma rays.

6. The method of claim 5 wherein obtaining said elemental composition further comprises decomposing said capture and inelastic gamma ray spectra using known basis functions for a set of elements.

7. The method of claim 6 further comprising determining a fraction of a particular element as a weighted average of fractions of said particular element determined from said capture spectrum and said inelastic spectrum.

8. The method of claim 1 wherein defining said set of possible constituents further comprises using geologic information.

9. The method of claim 8 wherein said geologic information is at least one of (i) basin wide, (ii) prospect based, and, (iii) based on sequence stratigraphy.

10. The method of claim 1 wherein defining said set of possible constituents further comprises use of petrophysical information.

11. The method of claim 1 wherein constrained optimization problem is a Linear Programming (LP) problem with inequality constraints.

12. The method of claim 11 wherein said LP problem further includes slack variables.

13. The method of claim 1 wherein said inequality constraints require that a fraction of each of said possible mineral constituents be non-negative.

14. The method of claim 1 wherein said earth formation comprises a carbonate, the method further comprising determining from said fraction for each of said constituents an amount of dolomitization of said carbonate.

15. The method of claim 1 wherein said composition comprises a mineralogical composition and wherein said constituents comprise a mineral composition.

16. An apparatus for determining a composition of an earth formation, the apparatus comprising:
   (a) a logging tool configured to be conveyed in a borehole in said earth formation; and
   (b) at least one processor configure to:
      (A) process measurements made by said logging tool to estimate an elemental composition of said earth formation, and
      (B) use a set of possible constituents for said earth formation to solve a constrained optimization problem to determine a fraction of each of said possible constituents that would give said obtained elemental composition, the determination not using an estimate of a shale volume.

17. The apparatus of claim 16 wherein said logging tool further comprises:
   (i) a source of neutrons configured to propagate neutrons into said earth formation, and
   (ii) at least one detector spaced apart from said source of neutrons configured to measure gamma rays resulting from interaction of said propagated neutrons with nuclei in said earth formation.

18. The apparatus of claim 17 wherein said at least one detector comprises at least two spaced-apart detectors.

19. The apparatus of claim 17 wherein said neutron source further comprises a pulsed neutron source.

20. The apparatus of claim 16 wherein said processor is configured to determine said elemental analysis by farther determining (i) a capture spectrum of gamma rays, and, (ii) an inelastic spectrum of gamma rays.

21. The apparatus of claim 20 wherein said processor is configured to obtain said elemental analysis by decomposing said capture and gamma ray spectra using known basis functions for a set of elements.

22. The apparatus of claim 21 wherein said processor is configured to determine a fraction of a particular element as a weighted average of fractions of said particular element determined from said capture spectrum and said inelastic spectrum.

23. The apparatus of claim 16 wherein said set of possible constituents is determined using geologic information.

24. The apparatus of claim 23 wherein said geologic information is at least one of (i) basin wide, (ii) prospect based, and, (iii) based on sequence stratigraphy.

25. The apparatus of claim 16 wherein said set of possible constituents is determined using petrophysical information.

26. The apparatus of claim 16 wherein said at least one processor comprises at least two processors.

27. The apparatus of claim 26 wherein one of said at least two processors is at a downhole location and another one of said at least two processors is at a surface location.

28. The apparatus of claim 16 further comprising a conveyance device configure to convey said logging tool into said borehole, the conveyance device select from of (i) a wireline, (ii) a slickline, and (iii) a drilling tubular.

29. The apparatus of claim 16 wherein constrained optimization problem is a Linear Programming (LP) problem with inequality constraints.

30. The apparatus of claim 29 wherein said LP problem further includes slack variables.

31. The apparatus of claim 16 wherein said inequality constraints require that a fraction of each of said possible constituents be non-negative.

32. The apparatus of claim 16 wherein said composition comprises a mineralogical composition and wherein said constituents comprise a mineral composition.

* * * * *